United States Patent
Jacobson

(10) Patent No.: US 10,159,252 B2
(45) Date of Patent: Dec. 25, 2018

(54) FUNGICIDAL COMPOUNDS AND COMPOSITIONS

(71) Applicant: AgroFresh Inc., Collegeville, PA (US)

(72) Inventor: Richard M. Jacobson, Chalfont, PA (US)

(73) Assignee: AGROFRESH INC., Philadelphia, PA (US)

( * ) Notice: Subject to any disclaimer, the term of this patent is extended or adjusted under 35 U.S.C. 154(b) by 0 days.

(21) Appl. No.: 15/626,583

(22) Filed: Jun. 19, 2017

(65) Prior Publication Data
US 2017/0280724 A1    Oct. 5, 2017

Related U.S. Application Data

(62) Division of application No. 15/040,388, filed on Feb. 10, 2016, now Pat. No. 9,730,454.

(60) Provisional application No. 62/115,174, filed on Feb. 12, 2015.

(51) Int. Cl.
| | | |
|---|---|---|
| *A01N 55/08* | (2006.01) | |
| *A23B 7/154* | (2006.01) | |
| *A23L 3/3463* | (2006.01) | |
| *C07F 5/02* | (2006.01) | |
| *A23B 4/20* | (2006.01) | |

(52) U.S. Cl.
CPC ............... *A01N 55/08* (2013.01); *A23B 4/20* (2013.01); *A23B 7/154* (2013.01); *A23L 3/3463* (2013.01); *C07F 5/02* (2013.01)

(58) Field of Classification Search
CPC .. A01N 55/08; C07F 5/02; A23B 4/20; A23B 7/154; A23L 3/3463
See application file for complete search history.

(56) References Cited

U.S. PATENT DOCUMENTS

| | | |
|---|---|---|
| 8,669,207 B1 | 3/2014 | Jacobson et al. |
| 9,138,001 B2 | 9/2015 | Maclean |
| 2009/0239824 A1 | 9/2009 | Lee et al. |
| 2009/0291917 A1 | 11/2009 | Akama et al. |
| 2011/0190235 A1 | 8/2011 | Chen et al. |
| 2011/0237547 A1 | 9/2011 | Mayer |
| 2014/0349853 A1* | 11/2014 | Maclean ............... A01N 55/08 504/357 |
| 2016/0235070 A1 | 8/2016 | Jacobson |

FOREIGN PATENT DOCUMENTS

| | | | |
|---|---|---|---|
| GB | 2314080 | 12/1997 | |
| WO | 1995/033754 | 12/1995 | |
| WO | WO-2014120715 A2 * | 8/2014 | ............ A01N 55/08 |

OTHER PUBLICATIONS

International Search Report and Written Opinion prepared for PCT/US2016/017326, dated Apr. 8, 2016, 9 pages.
Opposition Notice to Costa Rican Patent Application No. 2017-0414, submitted Apr. 27, 2018.

* cited by examiner

*Primary Examiner* — Yong L Chu
(74) *Attorney, Agent, or Firm* — Barnes & Thornburg LLP

(57) ABSTRACT

This invention is related to compounds and/or compositions useful against pathogens affecting meats, plants, or plant parts. In one embodiment, the provided compounds are products of certain oxaborole moieties. In a further embodiment, the compound comprises certain halogen substitutions on the boron atom. Delivery systems are also provided to take advantage of their fungicidal activity and/or volatile nature of these compounds and/or compositions. In another embodiment, the compounds disclosed have herbicidal activity.

19 Claims, 1 Drawing Sheet

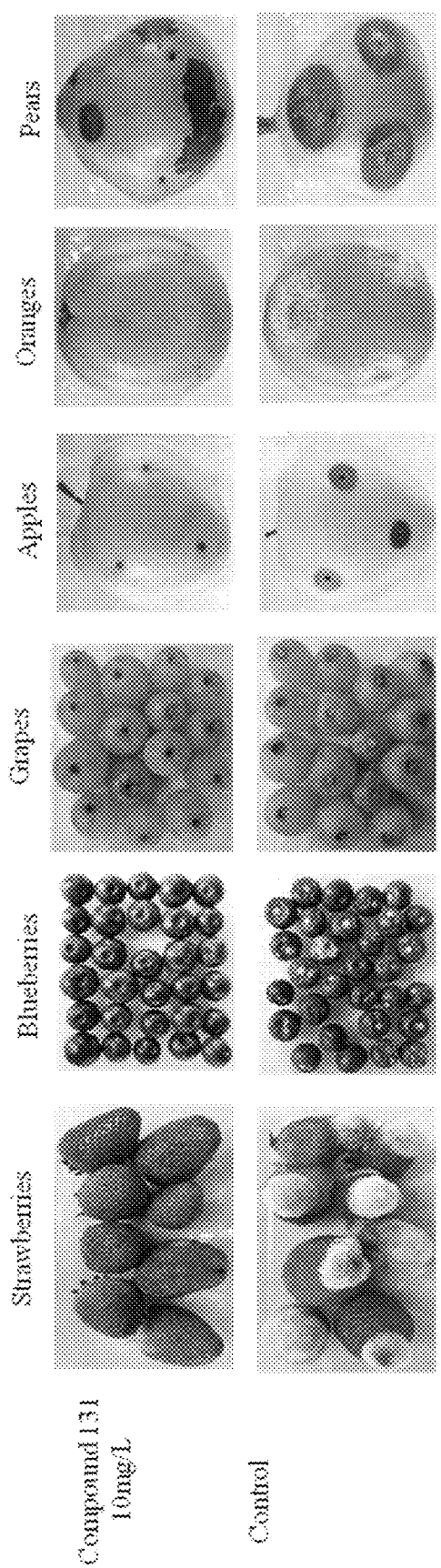

FUNGICIDAL COMPOUNDS AND COMPOSITIONS

CROSS REFERENCE TO RELATED APPLICATIONS

This application is a divisional of U.S. application Ser. No. 15/040,388, filed Feb. 10, 2016, now U.S. Pat. No. 9,730,454, which claims the benefit under 35 USC § 119(e) of U.S. Provisional Application Ser. No. 62/115,174, filed on Feb. 12, 2015, the entire disclosures of which are incorporated herein by reference.

BACKGROUND OF THE INVENTION

A number of compounds containing an oxaborole ring have been disclosed previously. However, there has been no teaching that these oxaborole compounds are volatile antimicrobial agents. In addition, there has been no teaching for modifying substituents on the boron atom while maintaining their antimicrobial activity and their use as contact or volatile fungicides.

Thus, there remains a need to develop new uses of various volatile antimicrobial agents and/or combinations with a volatile plant growth regulator, in particular for agricultural applications.

SUMMARY OF THE INVENTION

This invention is related to compounds and/or compositions useful against pathogens affecting meats, plants, or plant parts. In one embodiment, the provided compounds are products of certain oxaborole moieties. In a further embodiment, the compound comprises certain halogen substitutions on the boron atom. Delivery systems are also provided to take advantage of their fungicidal activity and/or volatile nature of these compounds and/or compositions. In another embodiment, the compounds disclosed have herbicidal activity.

In one aspect, provided is a compound having a structure of formula (A):

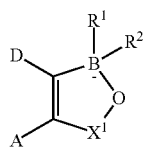

(A)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings; B is boron;

$R^1$ and $R^2$ are each independently halogen or nitrile;

$X^1$ is a group —$(CR^3R^4)_p$ wherein $R^3$ and $R^4$ are each independently hydrogen, $C_1$-$C_6$-alkyl, nitrile, nitro, aryl, arylalkyl or $R^3$ and $R^4$ together with the carbon atom to which they are attached form an alicyclic ring;

p is 1, 2, 3, or 4;

and agriculturally acceptable salts thereof.

In one embodiment, the compound of formula (A) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (A) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (A) is

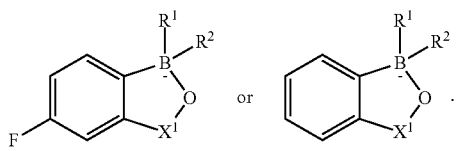

In a further embodiment, the compound of formula (A) is selected from the group consisting of

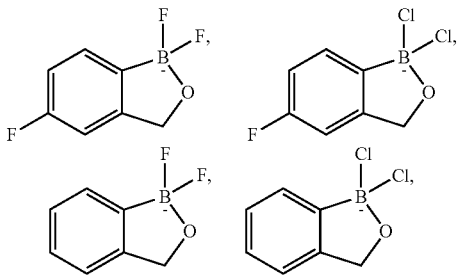

and combinations thereof. In another embodiment, the compound of formula (A) is selected from the group consisting of

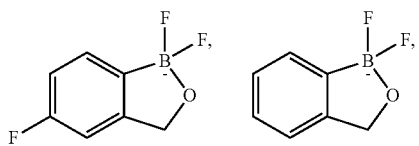

and combination thereof. In another embodiment, the compound of formula (A) is

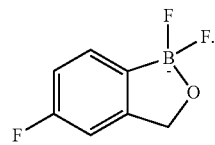

Additional oxaborole moieties are also disclosed previously in U.S. Pat. No. 5,880,188, the content of which is hereby incorporated by reference in its entirety.

In one aspect, provided is a compound having a structure of formula (B):

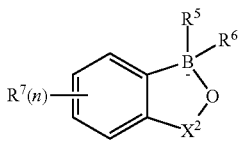

(B)

wherein $R^5$ and $R^6$ are each independently halogen or nitrile;

each $R^7$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X^2=(CR^7_2)_m$ where m=1, 2, 3, or 4; and $R^7$ is defined herein;

and agriculturally acceptable salts thereof.

In one embodiment, each $R^7$ is independently hydrogen, $C_1$-$C_6$-alkyl, nitrile, nitro, aryl, or arylalkyl. In another embodiment, $X^2=(CR^8R^9)_q$ wherein q=1, 2, 3, or 4; and $R^8$ and $R^9$ are each independently hydrogen, $C_1$-$C_6$-alkyl, nitrile, nitro, aryl, arylalkyl or $R^8$ and $R^9$ together with the carbon atom to which they are attached form an alicyclic ring.

In one embodiment, the compound of formula (B) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (B) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (B) is

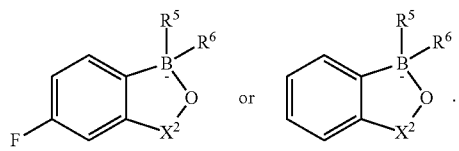

In a further embodiment, the compound of formula (B) is selected from the group consisting of

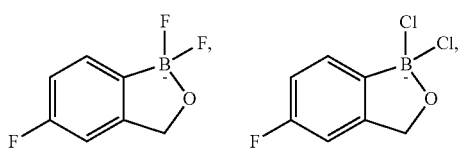

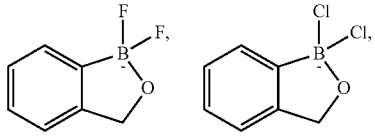

and combinations thereof. In another embodiment, the compound of formula (B) is selected from the group consisting of

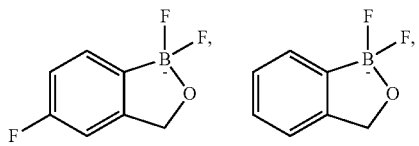

and combination thereof. In another embodiment, the compound of formula (B) is

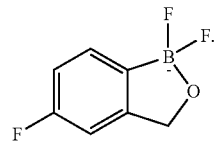

In another aspect, provided is a method of preparing a compound. The method comprises mixing at least one oxaborole compound with at least one reactant introducing a halogen or nitrile group to a (precursor) compound to generate compound(s) of formula (A) or (B).

BRIEF DESCRIPTION OF THE DRAWINGS

FIG. 1 shows the in vivo volatile antimicrobial activity of Sample 1 (compound 131; 10 mg/L headspace concentration) against 3 different fungal pathogens and 6 different hosts.

DETAILED DESCRIPTION OF THE INVENTION

This invention is based on surprising results that reaction of benzoxaborole compounds with potassium hydrogen difluoride or other reactants to generate a new class of compounds which can (1) possess volatile properties at room temperature; and (2) have antimicrobial activity against for example fungi, especially *Botrytis cinerea*. One example includes the product from reaction of 5-fluoro-1-hydroxy-2,1-benzoxaborole with potassium hydrogen difluoride, which shows excellent activity against *Botrytis cinerea*. Volatile antimicrobial agents (for example fungicides) have utility in postharvest disease control. Provided are methods using reaction of certain 1-hydroxybenzoxaborole compounds to form compounds having antimicrobial activity, and compounds and/or composition prepared by the methods disclosed.

Unless otherwise stated, the following terms used in this application, including the specification and claims, have the definitions given below. It must be noted that, as used in the specification and the appended claims, the singular forms "a," "an," and "the" include plural referents unless the context clearly dictates otherwise. The definition of standard chemistry terms may be found in reference works, including Carey and Sundberg, *Advanced Organic Chemistry* 4$^{th}$ ed., Vols. A (2000) and B (2001), Plenum Press, New York, N.Y.

As used herein, the phrase "moiety" refers to a specific segment or functional group of a molecule. Chemical moieties are often recognized chemical entities embedded in or appended to a molecule.

As used herein, the phrases "heteroatom" and "hetero-" refer to atoms other than carbon (C) and hydrogen (H). Examples of heteroatoms include oxygen (O), nitrogen (N), sulfur (S), silicon (Si), germanium (Ge), aluminum (Al) and boron (B).

As used herein, the phrases "halo" and "halogen" are interchangeable and refer to fluoro (—F), chloro (—Cl), bromo (—Br), and iodo (—I).

As used herein, the phrase "alkyl" refers to an unsubstituted or substituted, hydrocarbon group and can include straight, branched, cyclic, saturated and/or unsaturated features. Although the alkyl moiety may be an "unsaturated alkyl" moiety, which means that it contains at least one alkene or alkyne moiety, typically, the alkyl moiety is a "saturated alkyl" group, which means that it does not contain any alkene or alkyne moieties. Likewise, although the alkyl moiety may be a cyclic, typically the alkyl moiety is a non-cyclic group. Thus, in some embodiments, "alkyl" refers to an optionally substituted straight-chain, or optionally substituted branched-chain saturated hydrocarbon monoradical having from about one to about thirty carbon atoms in some embodiments, from about one to about fifteen carbon atoms in some embodiments, and from about one to about six carbon atoms in further embodiments. Examples of saturated alkyl radicals include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, t-butyl, n-pentyl, isopentyl, neopentyl, and n-hexyl, and longer alkyl groups, such as heptyl, and octyl. It should be noted that whenever it appears herein, a numerical range such as "1 to 6" refers to each integer in the given range; e.g., "1 to 6 carbon atoms" or "$C_{1-6}$" or "$C_1$-$C_6$" means that the alkyl group may consist of 1 carbon atom, 2 carbon atoms, 3 carbon atoms, 4 carbon atoms, 5 carbon atoms, and/or 6 carbon atoms, although the present definition also covers the occurrence of the term "alkyl" where no numerical range is designated.

As used herein, the phrase "substituted alkyl" refers to an alkyl group, as defined herein, in which one or more (up to about five, preferably up to about three) hydrogen atoms is replaced by a substituent independently selected from the substituent group defined herein.

As used herein, the phrases "substituents" and "substituted" refer to groups which may be used to replace another group on a molecule. Such groups are known to those of skill in the chemical arts and may include, without limitation, one or more of the following independently selected groups, or designated subsets thereof: halogen, —CN, —OH, —NO$_2$, —N$_3$, =O, =S, =NH, —SO$_2$, —NH$_2$, —COOH, nitroalkyl, amino, including mono- and di-substituted amino groups, cyanato, isocyanato, thiocyanato, isothiocyanato, guanidinyl, O-carbamyl, N-carbamyl, thiocarbamyl, uryl, isouryl, thiouryl, isothiouryl, mercapto, sulfanyl, sulfinyl, sulfonyl, sulfonamidyl, phosphonyl, phosphatidyl, phosphoramidyl, dialkylamino, diarylamino, diarylalkylamino; and the protected compounds thereof. The protecting groups that may form the protected compounds of the above substituents are known to those of skill in the art and may be found in references such as Wuts and Greene, *Greene's Protective Groups in Organic Synthesis*, 4$^{th}$ ed., John Wiley & Sons, Hoboken, N.J. (2007) and Kocienski, *Protective Groups*, 3$^{rd}$ ed., Thieme Verlag, New York, N.Y. (2005) which are incorporated herein by reference in their entirety.

As used herein, the phrase "alkoxy" refers to the group —O-alkyl, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, the phrases "cyclic" and "membered ring" refer to any cyclic structure, including alicyclic, heterocyclic, aromatic, heteroaromatic and polycyclic fused or non-fused ring systems as described herein. The term "membered" is meant to denote the number of skeletal atoms that constitute the ring. Thus, for example, pyridine, pyran, and pyrimidine are six-membered rings and pyrrole, tetrahydrofuran, and thiophene are five-membered rings.

As used herein, the phrase "aromatic" refers to a cyclic or polycyclic moiety having a conjugated unsaturated (4n+2) π electron system (where n is a positive integer), sometimes referred to as a delocalized π electron system.

As used herein, the phrase "aryl" refers to an optionally substituted, aromatic, cyclic, hydrocarbon monoradical of from six to about twenty ring atoms, preferably from six to about ten carbon atoms and includes fused (or condensed) and non-fused aromatic rings. A fused aromatic ring radical contains from two to four fused rings where the ring of attachment is an aromatic ring, and the other individual rings within the fused ring may be cycloalkyl, cycloalkenyl, cycloalkynyl, heterocycloalkyl, heterocycloalkenyl, heterocycloalkynyl, aromatic, heteroaromatic or any combination thereof. A non-limiting example of a single ring aryl group includes phenyl; a fused ring aryl group includes naphthyl, anthryl, azulenyl; and a non-fused bi-aryl group includes biphenyl.

As used herein, the phrase "substituted aryl" refers to an aryl group, as defined herein, in which one or more (up to about five, preferably up to about three) hydrogen atoms is replaced by a substituent independently selected from the group defined herein, (except as otherwise constrained by the definition for the aryl substituent).

As used herein, the phrase "heteroaryl" refers to an optionally substituted, aromatic, cyclic monoradical containing from about five to about twenty skeletal ring atoms, preferably from five to about ten ring atoms and includes fused (or condensed) and non-fused aromatic rings, and which have one or more (one to ten, preferably about one to about four) ring atoms selected from an atom other than carbon (i.e., a heteroatom) such as, for example, oxygen, nitrogen, sulfur, selenium, phosphorus or combinations thereof. The term heteroaryl includes optionally substituted fused and non-fused heteroaryl radicals having at least one heteroatom. A fused heteroaryl radical may contain from two to four fused rings where the ring of attachment is a heteroaromatic ring and the other individual rings within the fused ring system may be alicyclic, heterocyclic, aromatic, heteroaromatic or any combination thereof. The term heteroaryl also includes fused and non-fused heteroaryls having from five to about twelve skeletal ring atoms, as well as those having from five to about ten skeletal ring atoms. Examples of heteroaryl groups include, but are not limited to, acridinyl, benzo[1,3]dioxole, benzimidazolyl, benzindazolyl, benzoisooxazolyl, benzokisazolyl, benzofuranyl, benzofurazanyl, benzopyranyl, benzothiadiazolyl, benzothiazolyl, benzo[b]thienyl, benzothiophenyl, benzothiopyranyl, benzotriazolyl, benzoxazolyl, carbazolyl, carbolinyl, chromenyl, cinnolinyl, furanyl, furazanyl, furopyridinyl, furyl, imidazolyl, indazolyl, indolyl, indolidinyl, indolizinyl, isobenzofuranyl, isoindolyl, isoxazolyl, isoquinolinyl, isothiazolyl, naphthylidinyl, naphthyridinyl, oxadiazolyl, oxazolyl, phenoxazinyl, phenothiazinyl, phenazinyl, phenoxathiynyl, thianthrenyl, phenathridinyl, phenathrolinyl, phthalazinyl, pteridinyl, purinyl, pyrazyl, pyrazolyl, pyridyl, pyridinyl, pyridazinyl, pyrazinyl, pyrimidinyl, pyrimidyl, pyrrolyl, quinazolinyl, quinolinyl, quinoxalinyl, tetrazolyl, thiadiazolyl, thiazolyl, thienyl, triazinyl, (1,2,3,)- and (1,2,4)-triazolyl and the like, and their oxides where appropriate, such as for example pyridyl-N-oxide.

As used herein, the phrase "substituted heteroaryl" refers to a heteroaryl group, as defined herein, in which one or more (up to about five, preferably up to about three) hydrogen atoms is replaced by a substituent independently selected from the group defined herein.

As used herein, the phrase "leaving group" refers to a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyl/toluenesulfonyloxy, and thienyloxy, dihalophosphinoyloxy, optionally substituted benzyloxy, isopropyloxy, acyloxy, and the like. In some embodiments, a leaving group can be HC(O)—COOH or RC(O)—COOH, wherein R is a $C_1$-$C_6$ alkyl or substituted $C_1$-$C_6$ alkyl.

The compounds of the invention as described herein may be synthesized using standard synthetic techniques known to those of skill in the art or using methods known in the art in combination with methods described herein. The starting materials used for the synthesis of the compounds of the invention as described herein, can be obtained from commercial sources, such as Sigma-Aldrich Corp. (St. Louis, Mo.), Alfa Aesar (Ward Hill, Mass.) and Combi-Blocks, Inc. (San Diego, Calif.), or the starting materials can be synthesized. The compounds described herein, and other related compounds having different substituents can be synthesized using techniques and materials known to those of skill in the art, such as described, for example, in Smith, *March's Advanced Organic Chemistry* (2013) John Wiley & Sons, Hoboken, N.J.; Carey and Sundberg, *Advanced Organic Chemistry* 5th ed., Vols. A (2008) and B (2008) Spring Science+Business Media, LLC, New York, N.Y. and Wuts and Greene, *Greene's Protective Groups in Organic Synthesis*, 4th ed. (2007) John Wiley & Sons, Hoboken, N.J., (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. For example, the compounds described herein can be modified using various electrophiles or nucleophiles to form new functional groups or substituents.

In one aspect, provided is a compound having a structure of formula (A):

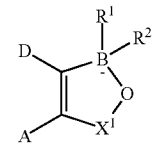

(A)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings; B is boron;

$R^1$ and $R^2$ are each independently halogen or nitrile;

$X^1$ is a group —$(CR^3R^4)_p$ wherein $R^3$ and $R^4$ are each independently hydrogen, $C_1$-$C_6$-alkyl, nitrile, nitro, aryl, arylalkyl or $R^3$ and $R^4$ together with the carbon atom to which they are attached form an alicyclic ring;

p is 1, 2, 3, or 4;

and agriculturally acceptable salts thereof.

In one embodiment, the compound is volatile. In another embodiment, the compound has antimicrobial activity.

In one embodiment, the compound of formula (A) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (A) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (A) is

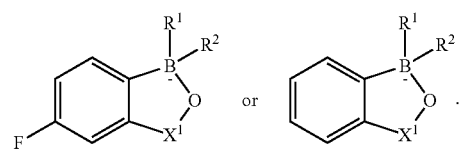

In a further embodiment, the compound of formula (A) is selected from the group consisting of

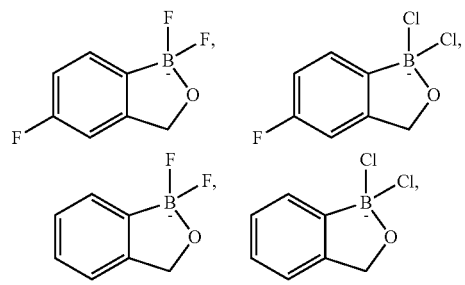

and combinations thereof. In another embodiment, the compound of formula (A) is selected from the group consisting of

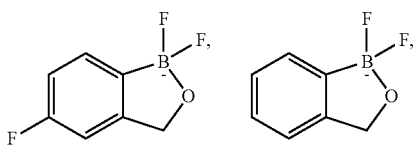

and combination thereof. In another embodiment, the compound of formula (A) is

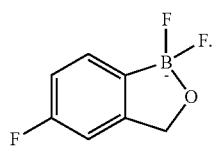

Additional oxaborole compounds useful for preparing compounds of formula (A) are also disclosed in U.S. Pat. No. 5,880,188, the content of which is hereby incorporated by reference in its entirety. In another aspect, provided is a mixture or composition comprising the compound of formula (A).

In another aspect, provided is a method of using a compound against pathogens affecting meats, plants, or plant parts, comprising contacting the meats, plants, or plant parts with an effective amount of the compound having a structure of formula (A):

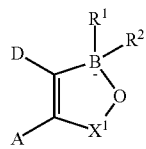

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings; B is boron;

$R^1$ and $R^2$ are each independently halogen or nitrile;

$X^1$ is a group —$(CR^3R^4)_p$ wherein $R^3$ and $R^4$ are each independently hydrogen, $C_1$-$C_6$-alkyl, nitrile, nitro, aryl, arylalkyl or $R^3$ and $R^4$ together with the carbon atom to which they are attached form an alicyclic ring;

p is 1, 2, 3, or 4;

and agriculturally acceptable salts thereof.

In one embodiment, the compound is volatile. In another embodiment, the compound is a fungicide. In another embodiment, the contacting comprises direct contact or contact as a volatile compound, i.e., via direct contact or via volatile activity. In a further embodiment, the contacting comprises application of a liquid formulation.

In one embodiment, the method of using a volatile compound against pathogens affecting meats, plants, or plant parts, comprises
  (a) providing a compound of formula (A) in gaseous form; and
  (b) contacting a meat, plant, or plant part with an effective amount of the compound of formula (A) in gaseous form.

In another embodiment, the method of using a volatile compound against pathogens affecting meats, plants, or plant parts, comprises
  (a) placing a meat, plant, or plant part in a container; and
  (b) introducing into the container and in contact with the meat, plant, or plant part an effective amount of the compound of formula (A) in gaseous form.

In another embodiment, the method of using a volatile compound against pathogens affecting meats, plants, or plant parts, comprises contacting the meats, plants, or plant parts with an atmosphere comprising an effective amount of the compound of formula (A) in gaseous form.

In one embodiment, the compound of formula (A) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (A) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (A) is

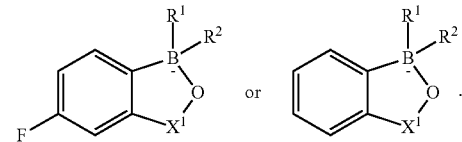

In a further embodiment, the compound of formula (A) is selected from the group consisting of

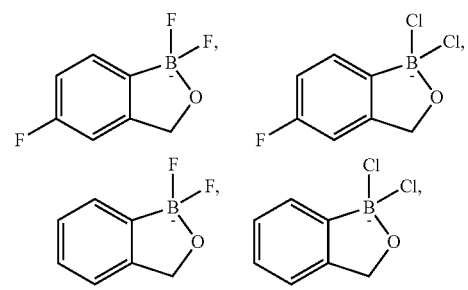

and combinations thereof. In another embodiment, the compound of formula (A) is selected from the group consisting of

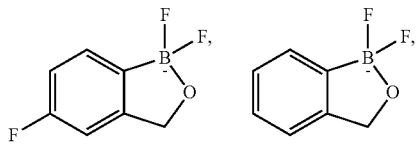

and combination thereof. In another embodiment, the compound of formula (A) is

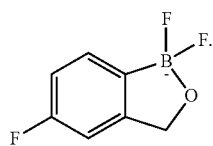

In another embodiment, the pathogen is selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp.

In another embodiment, the pathogen is selected from the group consisting of *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp. In another embodiment, the pathogen is selected from the group consisting of *Cryptosporidium* spp. and *Giardia* spp.

In another embodiment, the meats, plants, or plant parts are selected from the group consisting of corn, wheat, cotton, rice, soybean, and canola. In another embodiment, the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries (including strawberry, blueberry, raspberry, blackberry, currants and other types of berries).

In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during grading and sorting, treatment during palletization, in-box treatment, in-packaging treatment (e.g., in clamshell or similar), treatment during transportation (in transport trailer, marine container, airplane cargo, train car, or similar), and treatment during storage and/or throughout distribution network.

In another embodiment, the post-harvest treatment is performed in an enclosure. In a further embodiment, the enclosure is selected from the group consisting of a package, a box, a wrapped pallet, a sea container, a building, a room, and combinations thereof.

In another embodiment, the plants or plant parts comprise transgenic plants or transgenic plant parts. In another embodiment, the plants or plant parts are selected from the group consisting of barley, canola/oilseed rape, coffee, corn/maize, cotton, flax, grapevine, hops, mustard, nuts, oat, poppy, rice, rubber plant, rye, sunflower, sorghum, soybean, sugarcane, tea, tobacco, and wheat. In another embodiment, the plants or plant parts are selected from the group consisting of corn/maize, wheat, cotton, rice, soybean, and canola/oilseed rape. In another embodiment, the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries (including strawberry, blueberry, raspberry, blackberry, currants and other types of berries).

In another embodiment, the plants or plant parts are selected from the group consisting of flowers, fruit, vegetables, nursery, turf and ornamental crops. In a further embodiment, the fruit is selected from the group consisting of almond, apple, avocado, banana, berries (including strawberry, blueberry, raspberry, blackberry, currents and other types of berries), carambola, cherry, citrus (including oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. In a further embodiment, the vegetable is selected from the group consisting of asparagus, beet (for example sugar beet and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (for example sweet pepper, bell pepper, and hot pepper), potato, pumpkin, sweet potato, snap bean, squash, and tomato. In another embodiment, the nursery plant or flower or flower part is selected from the group consisting of baby's breath, carnation, dahlia, daffodil, geranium, gerbera, lily, orchid, peony, Queen Anne's lace, rose, snapdragon, or other cut-flowers or ornamental flowers, potted flowers, flower bulbs, shrub, deciduous or coniferous tree. In a further embodiment, the meat is selected from the group of beef, bison, chicken, deer, goat, turkey, pork, sheep, fish, shellfish, mollusks, or dry-cured meat products.

In one embodiment, the contacting comprises applying the compound by ways selected from the group consisting of spray, mist, thermal or non-thermal fogging, drench, gas treatment, incorporation into a wax coating, and combinations thereof. In a further embodiment, the gas treatment is selected from the group consisting of release from a sachet, release from a synthetic or natural film, fibrous material, and/or release from liner or other packaging materials, release from powder, release from a gas-releasing generator, release using a compressed or non-compressed gas cylinder, release from a droplet inside a box, wax coating, and combinations thereof.

In one aspect, provided is a compound having a structure of formula (B):

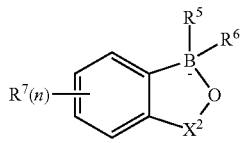
(B)

wherein $R^5$ and $R^6$ are each independently halogen or nitrile;

each $R^7$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X^2=(CR^7_2)_m$ where m=1, 2, 3, or 4; and $R^7$ is defined herein;

and agriculturally acceptable salts thereof.

In one embodiment, the compound is volatile. In another embodiment, the compound has antimicrobial activity.

In one embodiment, each $R^7$ is independently hydrogen, $C_1$-$C_6$-alkyl, nitrile, nitro, aryl, or arylalkyl. In another embodiment, $X^2=(CR^8R^9)_q$ wherein q=1, 2, 3, or 4; and $R^8$ and $R^9$ are each independently hydrogen, $C_1$-$C_6$-alkyl, nitrile, nitro, aryl, arylalkyl or $R^8$ and $R^9$ together with the carbon atom to which they are attached form an alicyclic ring.

In one embodiment, the compound of formula (B) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (B) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (B) is

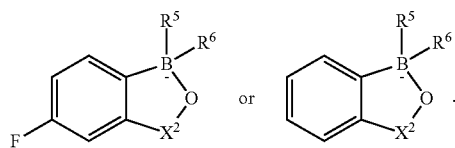

In a further embodiment, the compound of formula (B) is selected from the group consisting of

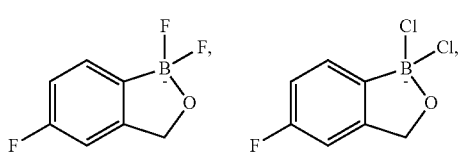

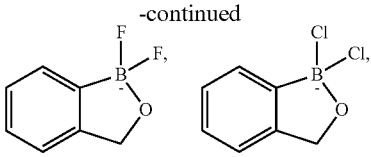
-continued and combinations thereof. In another embodiment, the compound of formula (A) is selected from the group consisting of

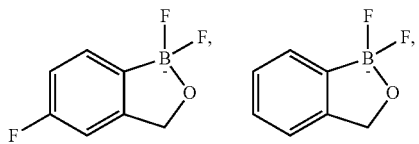

and combination thereof. In another embodiment, the compound of formula (A) is

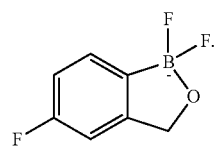

Additional oxaborole compounds useful for preparing compounds of formula (A) are also disclosed in U.S. Pat. No. 8,039,450, the content of which is hereby incorporated by reference in its entirety. In another aspect, provided is a mixture or composition comprising the compound of formula (B).

In another aspect, provided is a method of using a compound against pathogens affecting meats, plants, or plant parts, comprising contacting the meats, plants, or plant parts with an effective amount of the compound having a structure of formula (B):

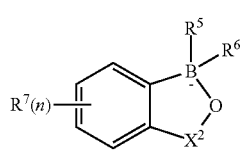
(B)

wherein $R^5$ and $R^6$ are each independently halogen or nitrile;

each $R^7$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X^2=(CR^7_2)_m$ where m=1, 2, 3, or 4; and $R^7$ is defined herein;

and agriculturally acceptable salts thereof.

In one embodiment, the compound is volatile. In another embodiment, the compound is a fungicide. In another embodiment, the contacting comprises direct contact or contact as a volatile compound, i.e., via direct contact or via volatile activity. In a further embodiment, the contacting comprises application of a liquid formulation.

In one embodiment, the method of using a volatile compound against pathogens affecting meats, plants, or plant parts, comprises
(a) providing a compound of formula (B) in gaseous form; and
(b) contacting a meat, plant, or plant part with an effective amount of the compound of formula (B) in gaseous form.

In another embodiment, the method of using a volatile compound against pathogens affecting meats, plants, or plant parts, comprises
(a) placing a meat, plant, or plant part in a container; and
(b) introducing into the container and in contact with the meat, plant, or plant part an effective amount of the compound of formula (B) in gaseous form.

In another embodiment, the method of using a volatile compound against pathogens affecting meats, plants, or plant parts, comprises contacting the meats, plants, or plant parts with an atmosphere comprising an effective amount of the compound of formula (B) in gaseous form.

In one embodiment, each $R^7$ is independently hydrogen, $C_1$-$C_6$-alkyl, nitrile, nitro, aryl, or arylalkyl. In another embodiment, $X^2=(CR^8R^9)_q$ wherein q=1, 2, 3, or 4; and $R^8$ and $R^9$ are each independently hydrogen, $C_1$-$C_6$-alkyl, nitrile, nitro, aryl, arylalkyl or $R^8$ and $R^9$ together with the carbon atom to which they are attached form an alicyclic ring.

In one embodiment, the compound of formula (B) is prepared from a (precursor) compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the compound of formula (B) is prepared from a (precursor) compound selected from the group consisting of 5-fluorobenzo[c][1,2]oxaborol-1(3H)-ol; 5-chlorobenzo[c][1,2]oxaborol-1(3H)-ol; benzo[c][1,2]oxaborol-1(3H)-ol; and combinations thereof.

In another embodiment, the compound of formula (B) is

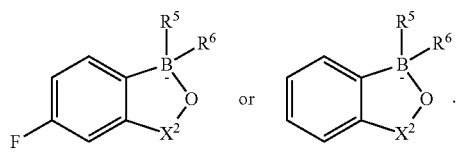

In a further embodiment, the compound of formula (B) is selected from the group consisting of

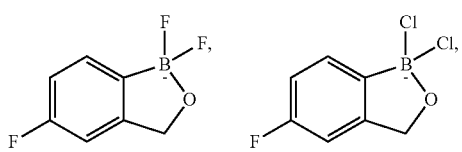

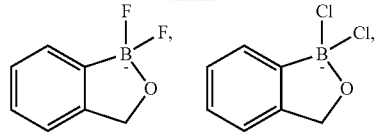

and combinations thereof. In another embodiment, the compound of formula (A) is selected from the group consisting of

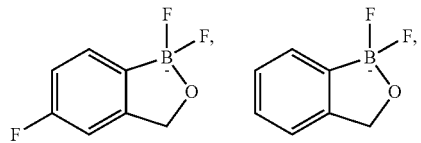

and combination thereof. In another embodiment, the compound of formula (A) is

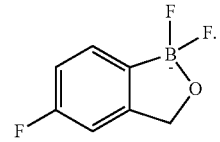

In another embodiment, the pathogen is selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp.

In another embodiment, the pathogen is selected from the group consisting of *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp. In another embodiment, the pathogen is selected from the group consisting of *Cryptosporidium* spp. and *Giardia* spp.

In another embodiment, the meats, plants, or plant parts are selected from the group consisting of corn, wheat, cotton, rice, soybean, and canola. In another embodiment, the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries (including strawberry, blueberry, raspberry, blackberry, currants and other types of berries).

In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during grading and sorting, treatment during palletization, in-box treatment, in-packaging treatment (e.g., in clamshell or similar), treatment during transportation (in transport trailer, marine container, airplane cargo, train car, or similar), and treatment during storage and/or throughout distribution network.

In another embodiment, the post-harvest treatment is performed in an enclosure. In a further embodiment, the enclosure is selected from the group consisting of a package, a box, a wrapped pallet, a sea container, a building, a room, and combinations thereof.

In another embodiment, the plants or plant parts comprise transgenic plants or transgenic plant parts. In another embodiment, the plants or plant parts are selected from the group consisting of barley, canola/oilseed rape, coffee, corn/maize, cotton, flax, grapevine, hops, mustard, nuts, oat, poppy, rice, rubber plant, rye, sunflower, sorghum, soybean, sugarcane, tea, tobacco, and wheat. In another embodiment, the plants or plant parts are selected from the group consisting of corn/maize, wheat, cotton, rice, soybean, and canola/oilseed rape. In another embodiment, the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries (including strawberry, blueberry, raspberry, blackberry, currants and other types of berries).

In another embodiment, the plants or plant parts are selected from the group consisting of flowers, fruit, vegetables, nursery, turf and ornamental crops. In a further embodiment, the fruit is selected from the group consisting of almond, apple, avocado, banana, berries (including strawberry, blueberry, raspberry, blackberry, currents and other types of berries), carambola, cherry, citrus (including oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. In a further embodiment, the vegetable is selected from the group consisting of asparagus, beet (for example sugar beet and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (for example sweet pepper, bell pepper, and hot pepper), potato, pumpkin, sweet potato, snap bean, squash, and tomato. In another embodiment, the nursery plant or flower or flower part is selected from the group consisting of baby's breath, carnation, dahlia, daffodil, geranium, gerbera, lily, orchid, peony, Queen Anne's lace, rose, snapdragon, or other cut-flowers or ornamental flowers, potted flowers, flower bulbs, shrub, deciduous or coniferous tree. In a further embodiment, the meat is selected from the group of beef, bison, chicken, deer, goat, turkey, pork, sheep, fish, shellfish, mollusks, or dry-cured meat products.

In one embodiment, the contacting comprises applying the compound by ways selected from the group consisting of spray, mist, thermal or non-thermal fogging, drench, gas treatment, incorporation into a wax coating, and combinations thereof. In a further embodiment, the gas treatment is selected from the group consisting of release from a sachet, release from a synthetic or natural film, fibrous material, and/or release from liner or other packaging materials, release from powder, release from a gas-releasing generator, release using a compressed or non-compressed gas cylinder, release from a droplet inside a box, wax coating, and combinations thereof.

In another aspect, provided is a method of preparing a compound. The method comprises mixing at least one oxaborole compound with at least one reactant comprising or introducing a halogen or nitrile group to generate compound of formula (A) or (B).

In one embodiment, the mixing is performed in presence of a solvent. In a further embodiment, the solvent comprises water, acetone, toluene, hexane, or combinations thereof. In another embodiment, the mixing is performed in presence of at least one catalyst. In a further embodiment, the catalyst is selected from the group consisting of amine, phosphine, heterocyclic nitrogen, ammonium, phosphonium, arsonium, sulfonium moieties, and combinations thereof. In another embodiment, the catalyst is selected from the group consisting of a phosphonium compound, an ammonium compound, chromium salts, amino compounds and combinations thereof. In another embodiment, the catalyst is selected from the group consisting of 2-methyl imidazole, 2-phenyl imidazole, an imidazole derivative, 1,8-diazabicyclo[5.4.0]undec-7-ene (DBU), and combinations thereof.

In another embodiment, the method further comprises evaporating the solvent by heating. In a further embodiment, the heating is performed at a temperature between 110° C. and 125° C.; between 100° C. and 150° C.; or between 80° C. and 200° C.

In another embodiment, the at least one oxaborole compound comprises a compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, the at least one reactant comprises potassium hydrogen difluoride.

Meats, plants, or plant parts may be treated in the practice of the present invention. One example is treatment of whole plants; another example is treatment of whole plants while they are planted in soil, prior to the harvesting of useful plant parts.

Any plants that provide useful plant parts may be treated in the practice of the present invention. Examples include plants that provide flowers, fruits, vegetables, and grains.

As used herein, the phrase "plant" includes dicotyledonous plants and monocotyledonous plants. Examples of dicotyledonous plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale. Examples of fruit include banana, pineapple, oranges, grapes, grapefruit, watermelon, melon, apples, peaches, pears, kiwifruit, mango, nectarines, guava, persimmon, avocado, lemon, fig, and berries. Examples of flowers include baby's breath, carnation, dahlia, daffodil, geranium, gerbera, lily, orchid, peony, Queen Anne's lace, rose, snapdragon, or other cut-flowers or ornamental flowers, potted-flowers, and flower bulbs.

Those skilled in the art would understand certain variation can exist based on the disclosure provided. Thus, the following examples are given for the purpose of illustrating the invention and shall not be construed as being a limitation on the scope of the invention or claims.

EXAMPLES

Example 1

Preparation of Sample 1

Aqueous potassium hydrogen difluoride solution (Sigma-Aldrich Chemical, 3.0 Molar (M) solution; 4.01 grams (g)) is added to 1-hydroxy-5-fluoro-1,3-dihydro-2,1-benzoxaborole (1.6 g, 10.54 millimoles (mmol)) dissolved in acetone (5 g). The mixture is mixed for 30 minutes (min), whereupon the acetone is removed by rotary evaporation, and the water is removed by azeotropic distillation with toluene using a Dean-Stark trap. The resulting solid suspension is filtered, washed with diethyl ether and air dried to give the desired difluoroboronate salt, potassium 1,1,5-trifluoro-1,3-dihydro-2,1-benzoxaborolate salt (2.02 g, 95%). NMR spectra are consistent with the proposed structure.

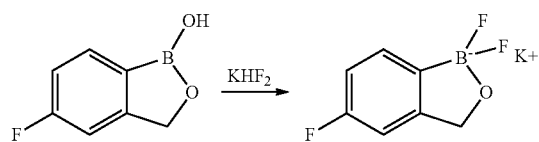

Example 2

In Vitro Analysis

A 12-well microtiter plate (6.5 milliliter (mL) volume per well) is used for the in vitro inhibition assay for volatile antimicrobial compound of Sample 1 (see Example 1) against two plant fungal pathogens. A 3-mL volume of half-strength Potato Dextrose Agar (PDA) is added to each well. After cooling, 1 microliter (µL) of 1×10⁵ spores per mL of *Botrytis cinerea* (*B. cinerea*) or *Penicillium expansum* (*P. expansum*) suspension is spotted to the center of the agar. A Whatman #1 filter disk (Cat. No. 1001-0155) is placed, in duplicate, on the underside of a polyethylene polymerase chain reaction (PCR) plate sealing film.

TABLE 1

Concentration (MIC) and $EC_{50}$ (mg/L) of Sample 1 applied as a volatile fungicide against two fungal plant pathogens.

| Concentration (mg/L) | B. cinerea | P. expansum |
|---|---|---|
| 35.7 | 100 | 100 |
| 17.9 | 100 | 100 |
| 8.9 | 100 | 100 |
| 4.5 | 100 | 100 |

TABLE 1-continued

Concentration (MIC) and $EC_{50}$ (mg/L) of Sample 1 applied as a volatile fungicide against two fungal plant pathogens.

| Concentration (mg/L) | B. cinerea | P. expansum |
|---|---|---|
| 2.2 | 100 | 73 |
| 1.1 | 100 | 56.2 |
| 0.6 | 64.8 | 12.9 |
| 0.3 | 0 | −8.2 |
| 0.1 | 0 | −3.3 |
| 0.07 | 0 | −1.9 |
| 0.03 | 0 | −2.7 |
| MIC | 1.1 | 4.5 |
| $EC_{50}$ | 0.5 | 1.2 |

For determination of the minimum inhibitory concentration (MIC), the test compound is diluted in acetone, and the appropriate amount of compound added to disks in a dose dependent manner to achieve a final headspace concentration of 35.7 to 0.03 milligrams per liter (mg/L). The acetone is permitted to evaporate for 5 min. The headspace around the inoculum is then sealed inside the well by the film with the adhering disk containing the fungicide. The plates are inverted, placed over the treated disks and sealed to prevent any of the chemical from flaking from the disk and falling onto the inoculated agar. After 3 days (d) of storage at 23° C., cultures are evaluated for percent growth relative to control. Results are summarized in Table 1 showing the ability of benzoxaborole compound of Sample 1 to control the growth of two fungal plant pathogens through volatile activity.

Example 3

In Vivo Analysis Using Fruits

To assess the in vivo activity of volatile antimicrobial compound of Sample 1 (see Example 1) in fruit, a volatile bioassay is developed using apple, pear, orange, strawberry, grape and blueberry. Two apples, two oranges, two pears, eight strawberries, sixteen grapes or thirty blueberries (per rep, in duplicate) are placed in a clamshell with the stem end facing up for all fruits except for strawberry (stem end facing downwards). A fresh wound is inoculated with 20 µL 1×10⁶ per mL *Penicillium expansum* (*P. expansum*) spore suspension (apple and pear), 20 µL×1×10⁶ per mL *Penicillium digitatum* (*P. digitatum*) spore suspension (orange), and 20 µL×1×10⁶ (strawberry and grape) or 10 µL (blueberry) of 1×10⁵ per mL *Botrytis cinerea* (*B. cinerea*) spore suspension. The clamshells are placed inside a 117 L Rubbermaid storage box (Cat #2244), and the lids closed.

Sample 1, prepared according to Example 1 and dissolved in acetone, is pipetted onto a cotton strip, where the acetone is allowed to evaporate for 5 min, and then introduced into the container by a sublimation device (copper tube heated to 200° C. with fan flow at 0.5 liters per minute (L/min)) to achieve a final headspace concentration of 10 mg/L). The containers are then held for 3 d at 21° C. After treatment, the fruits are held for an additional 3 d at 21° C., then evaluated for disease incidence (millimeter (mm) diameter of browning or water-soaked lesions) and pathogen sporulation (mm diameter) for apple, pear and orange, as well as *Botrytis cinerea* disease incidence (%) and severity (0 to 4) for strawberry, grape and blueberry. Results are summarized in Table 2 showing good in vivo antimicrobial control of three fungal pathogens on six different hosts when applied as a volatile fungicide. Results are also depicted in FIG. 1.

TABLE 2

Effects of subliming Sample 1 as reflected by incidence and severity of *B. cinerea* on strawberry, grape and blueberry, and severity of *Penicillium* spp. on oranges, apples and pears as depicted by water soaked lesions, browning and sporulation after a 3 day treatment plus an additional 3 days at 21° C.

| Treatments | Incidence (%) | | | Severity (0-4) | | |
|---|---|---|---|---|---|---|
| | Strawberry | Blueberry | Grape | Strawberry | Blueberry | Grape |
| Sample 1 | 6.3 | 5.0 | 23.3 | 0.03 | 0.06 | 0.12 |
| Control | 100.0 | 100.0 | 80.0 | 3.63 | 2.18 | 0.88 |

| | Water soaked lesion (mm) | Browning (mm) | | Sporulation (mm) | | |
|---|---|---|---|---|---|---|
| | Orange | Apple | Pear | Apple | Orange | Pear |
| Sample 1 | 12.7 | 4.8 | 5.3 | 7.3 | 0.0 | 4.3 |
| Control | 50.5 | 11.5 | 23.3 | 33.2 | 4.8 | 12.5 |

I claim:

1. A method of using a compound against pathogens affecting meats, plants, or plant parts, comprising contacting the meats, plants, or plant parts with an effective amount of the compound having a structure of formula (A):

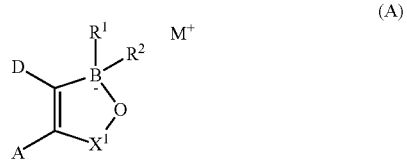

(A)

wherein

A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

$R^1$ and $R^2$ are each independently halogen or nitrile;

$X^1$ is a group —$(CR^3R^4)_p$ wherein $R^3$ and $R^4$ are each independently hydrogen, $C_1$-$C_6$-alkyl, nitrile, nitro, aryl, arylalkyl or $R^3$ and $R^4$ together with the carbon atom to which they are attached form an alicyclic ring;

p is 1, 2, 3, or 4;

$M^+$ is a salt counterion;

and agriculturally acceptable salts thereof, and wherein the pathogen is *Penicillium expansum* (*P. expansum*), *Penicillium digitatum* (*P. digitatum*), or *Botrytis cinerea* (*B. cinerea*).

2. The method of claim 1, wherein the compound of formula (A) is

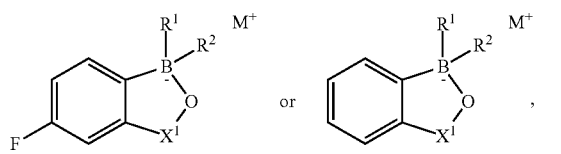

or an agriculturally acceptable salt thereof.

3. The method of claim 1, wherein the compound of formula (A) is selected from the group consisting of

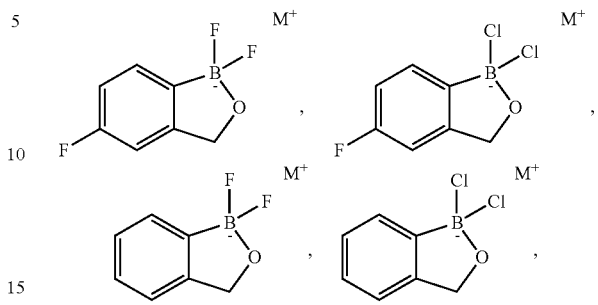

an agriculturally acceptable salt thereof, and combinations thereof.

4. The method of claim 1, wherein the meats, plants, or plant parts are selected from the group consisting of corn, wheat, cotton, rice, soybean, and canola.

5. The method of claim 1, wherein the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries.

6. A method of using a compound against pathogens affecting meats, plants, or plant parts, comprising contacting the meats, plants, or plant parts with an effective amount of the compound having a structure of formula (B):

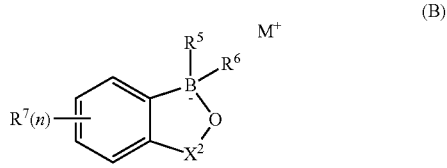

(B)

wherein $R^5$ and $R^6$ are each independently halogen or nitrile;

each $R^7$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X^2$=$(CR^7_2)_m$ where m=1, 2, 3, or 4; and $R^7$ is defined herein;

$M^+$ is a salt counterion;

and agriculturally acceptable salts thereof, and wherein the pathogen is *Penicillium expansum* (*P. expansum*), *Penicillium digitatum* (*P. digitatum*), or *Botrytis cinerea* (*B. cinerea*).

7. The method of claim 6, wherein the compound of formula (B) is

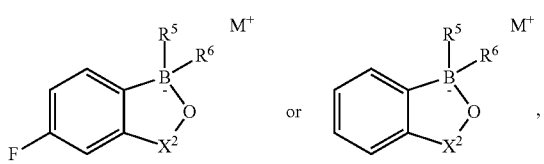

or an agriculturally acceptable salt thereof.

8. The method of claim 6, wherein the meats, plants, or plant parts are selected from the group consisting of corn, wheat, cotton, rice, soybean, and canola.

9. The method of claim 6, wherein the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries.

10. The method of claim 1, wherein p is 1 or 2.

11. The method of claim 1, wherein the step of contacting comprises applying the compound by a way selected from the group consisting of spray, mist, thermal or non-thermal fogging, drench, gas treatment, incorporation into a wax coating, and combinations thereof.

12. The method of claim 11, wherein the gas treatment is selected from the group consisting of release from a sachet, release from a synthetic or natural film, release from a fibrous material, release from a liner or other packaging materials, release from a powder, release from a gas-releasing generator, release using a compressed or non-compressed gas cylinder, release from a droplet inside a box, release from wax coating, and combinations thereof.

13. The method of claim 6, wherein the plants or plant parts are selected from the group consisting of flowers, fruit, vegetables, nursery, turf, and ornamental crops.

14. The method of claim 6, wherein m is 1 or 2.

15. The method of claim 6, wherein the step of using comprises applying the compound by a way selected from the group consisting of spray, mist, thermal or non-thermal fogging, drench, gas treatment, incorporation into a wax coating, and combinations thereof.

16. The method of claim 15, wherein the gas treatment is selected from the group consisting of release from a sachet, release from a synthetic or natural film, release from a fibrous material, release from a liner or other packaging materials, release from a powder, release from a gas-releasing generator, release using a compressed or non-compressed gas cylinder, release from a droplet inside a box, release from wax coating, and combinations thereof.

17. The method of claim 1, wherein the pathogen is *P. expansum.*

18. The method of claim 1, wherein the pathogen is *P. digitatum.*

19. The method of claim 1, wherein the pathogen is *B. cinerea.*

* * * * *